United States Patent
Spyrou

(10) Patent No.: US 11,154,028 B2
(45) Date of Patent: Oct. 26, 2021

(54) COTTON VARIETY GW-13-1409

(71) Applicant: Golden West Research Ltd., Rousse (BG)

(72) Inventor: Spyridon Spyrou, Athens (GR)

(73) Assignee: Golden West Research Ltd., Rousse (BG)

( * ) Notice: Subject to any disclaimer, the term of this patent is extended or adjusted under 35 U.S.C. 154(b) by 0 days.

(21) Appl. No.: 16/296,981

(22) Filed: Mar. 8, 2019

(65) Prior Publication Data

US 2020/0281149 A1 Sep. 10, 2020

(51) Int. Cl.
*A01H 6/60* (2018.01)
*A01H 5/10* (2018.01)

(52) U.S. Cl.
CPC .............. *A01H 6/604* (2018.05); *A01H 5/10* (2013.01)

(58) Field of Classification Search
CPC ..................................................... A01H 6/604
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 12/1996 | Hunsperger et al. | |
| 5,763,755 A | 6/1998 | Carlone | |
| 5,850,009 A | 12/1998 | Kevern | |
| 2007/0056062 A1 * | 3/2007 | Reid | A01H 5/10 800/314 |

OTHER PUBLICATIONS

Liu et al Plant Biology vol. 12 pp. 895-902 (Year: 2010).*
Allard, R.W., 1960, Selection under self-fertilization, Principles of Plant Breeding, John Wiley & Sons, Inc., p. 55.
Eshed, et al., 1996, Less-than-additive epistatic interactions of quantitative trait loci in tomato, Genetics, 143:1807-1817.
Fehr, W.R., 1987, Principles of cultivar development, Theory and Technique, McGraw-Hill, Inc. 1:31-33.
Kraft, et al., 2000, Linkage disequilibrium and fingerprinting in sugar beet, Theor. Appl. Genet., 101:323-326.
Mishra, et al., 2003, Development of a highly regenerable elite acala cotton (*Gossypium hirsutum* cv. Maxxa)—a step towards genotype-independent regeneration, Plant Cell, Tissue and Organ Culture, 73:21-35.
Poehlman, J.M. and Sleper, D.A., Breeding Field Crops, 4th Ed. (1995), Iowa State University Press, Ames, Iowa, p. 473.
Sahkanokho, et al., 2001, Induction of highly embryogenic calli and plant regeneration in upland (*Gossypium hirsutum* L.) and pima {*Gossypium barbadense* L.) cottons, Crop Sci., 41: 1235-1240.
Wilson, F. Douglas, 1989, Yield, earliness, and fiber properties of cotton carrying combined traits for pink bollworm resistance, Crop Sci., 29:7-12.
Fryxell, P.A., 1984, Taxonomy and Germplasm resources, Cotton Monograph 24, Amer. Soc. Agron., Kohel, R.J. and C.F. Lewis, Eds., pp. 53-54.
Ragot, M., et al., 1994, Marker-assisted backcrossing: a practical example. Techniques et utilizations des marqueurs moleculaires, Montpellier, France, pp. 45-56.
Young, N.D. and Tanksley, S.D., 1989, RFLP analysis of the size of chromosomal segments retained around the Tm-2 locus of tomato during backcross breeding, Theor. Appl. Genet., 77:353-359.
Zeven, A.C., et al., 1983, Investigation of linkage drag in near isogenic lines of wheat by testing for seedling reaction to races of stem rust, leaf rust and yellow rust, Euphytica, 32:319-327.

* cited by examiner

*Primary Examiner* — David H Kruse
(74) *Attorney, Agent, or Firm* — Weatherly IP Solutions, LLC; Barbara Campbell

(57) ABSTRACT

A cotton cultivar designated GW-13-1409 is disclosed. Embodiments include the seeds of cotton GW-13-1409, the plants of cotton GW-13-1409, to plant parts of cotton GW-13-1409, and methods for producing a cotton plant produced by crossing cotton GW-13-1409 with itself or with another cotton variety. Embodiments include methods for producing a cotton plant containing in its genetic material one or more genes or transgenes and the transgenic cotton plants and plant parts produced by those methods. Embodiments also relate to cotton cultivars, breeding cultivars, plant parts, and cells derived from cotton GW-13-1409, methods for producing other cotton cultivars, lines or plant parts derived from cotton GW-13-1409, and the cotton plants, varieties, and their parts derived from use of those methods. Embodiments further include hybrid cotton seeds, plants, and plant parts produced by crossing GW-13-1409 with another cotton cultivar.

20 Claims, No Drawings

COTTON VARIETY GW-13-1409

BACKGROUND

All publications cited in this application are herein incorporated by reference.

Cotton is an important and valuable crop. There are about 50 different species belong to the genus *Gossypium*. Commercial species of cotton plants are *G. hirsutum, G. barbadense, G. arboreum* and *G. herbaceum*. The goal in breeding new varieties of cotton include important traits include higher fiber (lint) yield, earlier maturity, improved fiber quality, resistance to diseases and insects, tolerance to drought and heat, and improved agronomic traits. To accomplish this goal, the breeder must select and develop plants that have traits that result in superior cotton varieties.

The foregoing examples of the related art and limitations related therewith are intended to be illustrative and not exclusive. Other limitations of the related art will become apparent to those of skill in the art upon a reading of the specification.

SUMMARY

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

One embodiment relates to seed of the cotton variety GW-13-1409. Another embodiment also relates to plants produced by growing the seed of the cotton variety GW-13-1409, as well as the derivatives of such plants. As used herein, the term "plant" includes plant cells, plant protoplasts, plant cells of a tissue culture from which cotton plants can be regenerated, plant calli, plant clumps, and plant cells that are intact in plants or parts of plants, such as pollen, flowers, seeds, bolls, leaves, stems, and the like.

Another embodiment relates to a tissue culture of regenerable cells of the cotton variety GW-13-1409, as well as plants regenerated therefrom, wherein the regenerated cotton plant is capable of expressing all of the morphological and physiological characteristics of a plant grown from the cotton seed designated GW-13-1409. One embodiment provides for regenerable cells for use in tissue culture of cotton cultivar GW-13-1409. The tissue culture can be capable of regenerating plants having the physiological and morphological characteristics of the cotton cultivar GW-13-1409 as described herein, and of regenerating plants having substantially the same genotype as the cotton plant of the embodiments. The regenerable cells in such tissue cultures can be from embryos, a plant cell, protoplasts, meristematic cells, callus, pollen, leaves, anthers, ovules, pistils, roots, root tips, flowers, seeds, pods, bolls, fiber, leaves, gossypol glands, or stems. Still further, the embodiments provide for cotton plants regenerated from the tissue cultures of the embodiments.

Another embodiment is a cotton plant of the cotton variety GW-13-1409 further comprising a single locus conversion. In one embodiment, the cotton plant is defined as comprising the single locus conversion and otherwise capable of expressing all of the morphological and physiological characteristics of the cotton variety GW-13-1409. In other embodiments, the single locus conversion may comprise a transgenic gene which has been introduced by genetic transformation into the cotton variety GW-13-1409 or a progenitor thereof. A transgenic or non-transgenic single locus conversion can also be introduced by backcrossing, as is well known in the art. In other embodiments, the single locus conversion may comprise a dominant or recessive allele. The locus conversion may confer potentially any desired trait upon the plant as described herein. In other embodiments, a locus conversion may confer one or more traits such as, for example, male sterility, herbicide tolerance, insect resistance, disease resistance, waxy starch, modified fatty acid metabolism, modified phytic acid metabolism, modified carbohydrate metabolism and modified protein metabolism. In other embodiments, a trait that confers herbicide resistance may confer resistance to herbicides such as, for example, imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid synthase-inhibiting herbicides, bromoxynil, nicosulfuron, 2,4-dichlorophenoxyacetic acid (2,4-D), dicamba, quizalofop-p-ethyl, glyphosate, or glufosinate.

Another embodiment relates to a first generation ($F_1$) hybrid cotton seed produced by crossing a plant of the cotton variety GW-13-1409 to a second cotton plant. Also included in the embodiment are the $F_1$ hybrid cotton plants grown from the hybrid seed produced by crossing the cotton variety GW-13-1409 to a second cotton plant. Still further included in the embodiments are the seeds of an $F_1$ hybrid plant produced with the cotton variety GW-13-1409 as one parent, the second generation ($F_2$) hybrid cotton plant grown from the seed of the $F_1$ hybrid plant, and the seeds of the $F_2$ hybrid plant.

In an embodiment, a composition is provided comprising a seed of cotton variety GW-13-1409 comprised in plant seed growth media. In one embodiment, the plant seed growth media is a soil or synthetic cultivation medium. In another embodiment, the growth medium may be comprised in a container or may, for example, be soil in a field. Plant seed growth media are well-known to those of skill in the art and include, but are in no way limited to, soil or synthetic cultivation medium. Plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Another embodiment is a method of producing cotton seeds comprising crossing a plant of the cotton variety GW-13-1409 to any second cotton plant, including itself or another plant of the variety GW-13-1409. In another embodiment, the method of crossing comprises the steps of a) planting seeds of the cotton variety GW-13-1409; b) cultivating cotton plants resulting from said seeds until said plants bear flowers; c) allowing fertilization of the flowers of said plants; and, d) harvesting seeds produced from said plants.

Another embodiment is a method of producing hybrid cotton seeds comprising crossing the cotton variety GW-13-1409 to a second, distinct cotton plant which is non-isogenic to the cotton variety GW-13-1409. In another embodiment, the crossing comprises the steps of a) planting seeds of cotton variety GW-13-1409 and a second, distinct cotton plant, b) cultivating the cotton plants grown from the seeds until the plants bear flowers; c) cross-pollinating a flower on one of the two plants with the pollen of the other plant, and d) harvesting the seeds resulting from the cross-pollinating.

Another embodiment is a method for developing a cotton plant in a cotton breeding program comprising: obtaining a cotton plant, or its parts, of the variety GW-13-1409; and b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments, the cotton plant of variety GW-13-1409 is used as the male or female parent.

Another embodiment is a method of producing a cotton plant derived from the cotton variety GW-13-1409, the method comprising the steps of: (a) preparing a progeny plant derived from cotton variety GW-13-1409 by crossing a plant of the cotton variety GW-13-1409 with a second cotton plant; and (b) crossing the progeny plant with itself or a second plant to produce a progeny plant of a subsequent generation which is derived from a plant of the cotton variety GW-13-1409. In one embodiment, the method further comprises: (c) crossing the progeny plant of a subsequent generation with itself or a second plant; and (d) repeating steps (b) and (c) for at least 2-10 additional generations to produce an inbred cotton plant derived from the cotton variety GW-13-1409. Another embodiment is a plant produced by this and the other methods of the embodiment. Plant variety GW-13-1409-derived plants produced by this and the other methods of the embodiments described herein may, in other embodiments, be further defined as comprising the traits of plant variety GW-13-1409 given in all of the Tables herein.

Another embodiment includes a method for developing a cotton plant in a plant breeding program, comprising applying plant breeding techniques comprising crossing, outcrossing, recurrent selection, mutation breeding, wherein said mutation breeding selects for a mutation that is spontaneously or naturally induced or artificially induced, backcrossing, pedigree breeding, marker enhanced selection, haploid/double haploid production, or transformation to the cotton plant of GW-13-1409, or its parts, wherein application of said techniques results in development of a cotton plant.

A method of introducing a mutation into the genome of a cotton plant GW-13-1409, said method comprising mutagenesis of the plant, or plant part thereof of GW-13-1409 wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

Definitions

In addition to the exemplary aspects and embodiments described above, further aspects and embodiments will become apparent by study of the following descriptions.

In the description and tables which follow, a number of terms are used. In order to provide a clear and consistent understanding of the specification and claims, including the scope to be given such terms, the following definitions are provided:

Seed Index. As used herein "Seed Index" is a measurement in grams of the total weight of one hundred seeds.

Disease resistance. As used herein, the term "disease resistance" is defined as the ability of plants to restrict the activities of a specified pest, such as an insect, fungus, virus, or bacterial.

Disease tolerance. As used herein, the term "disease tolerance" is defined as the ability of plants to endure a specified pest (such as an insect, fungus, virus or bacteria) or an adverse environmental condition and still perform and produce in spite of this disorder.

Essentially all of the physiological and morphological characteristics. Essentially all of the physiological and morphological characteristics means a plant having essentially all of the physiological and morphological characteristics of the recurrent parent, except for the characteristics derived from the converted trait.

Elongation (Elong). As used herein, the term "elongation" is defined as the measure of elasticity of a bundle of fibers as measured by HVI.

Fiber strength (STR). As used herein, the term "fiber strength" is defined as the force required to break a bundle of fibers as measured in grams per millitex on the HVI.

Fruiting nodes. As used herein, the term "fruiting nodes" is defined as the number of nodes on the main stem from which arise branches which bear fruit or bolls.

Gin turnout (GTO). As used herein, the term "gin turnout" is defined as a fraction of lint in a machine harvested sample of seed cotton (lint, seed, and trash).

Kleistogamia or cleistogamy. As used herein "Kleistogamia" or "cleistogamy" is a trait of certain plants to propagate by using non-opening, self-pollinating flowers.

Length (LEN). As used herein, the term "length" is defined as 2.5% span length in inches of fiber as measured by High Volume Instrumentation (HVI).

Lint/boll. As used herein, the term "lint/boll" is the weight of lint per boll.

Lint index. As used herein, the term "lint index" refers to the weight of lint per seed in milligrams.

Lint percent. As used herein, the term "lint percent" is defined as the lint (fiber) fraction of seed cotton (lint and seed). Also known as lint turnout.

Lint yield. As used herein, the term "lint yield" is defined as the measure of the quantity of fiber produced on a given unit of land.

Maturity. As used herein, the term "maturity" is defined as the HVI machine rating which refers to the degree of development of thickening of the fiber cell wall relative to the perimeter or effective diameter of the fiber.

Maturity rating (MAT). As used herein, the term "maturity rating" is defined as a visual rating of plants of a variety, when 50% of all plants in two middle rows have at least one open boll.

Micronaire (MIC). As used herein, the term "micronaire" is defined as a measure of the fineness of the fiber. Within a cotton cultivar, micronaire is also a measure of maturity. Micronaire differences are governed by changes in perimeter or in cell wall thickness, or by changes in both. Within a cultivar, cotton perimeter is fairly constant and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:

| | | |
|---|---|---|
| Below 2.9 | Very fine | Possible small perimeter but mature (good fiber), or large perimeter but immature (bad fiber). |
| 2.9 to 3.7 | Fine | Various degrees of maturity and/or perimeter. |
| 3.8 to 4.6 | Average | Average degree of maturity and/or perimeter. |
| 4.7 to 5.5 | Coarse | Usually fully-developed (mature), but larger perimeter. |
| 5.6+ | Very coarse | Fully-developed, large-perimeter fiber. |

Plant height. As used herein, the term "plant height" is defined as the average height in inches or centimeters of a group of plants.

Stremma (str). As used herein, the term "stremma" is defined as 1/10 of a hectare.

Vegetative nodes. As used herein, the term "vegetative nodes" is defined as the number of nodes from the cotyledonary node to the first fruiting branch on the main stem of the plant.

Weight of boll. As used herein, the term "weight of boll" refers to the weight of a cotton boll in grams.

Wilt %. Means the percentage of plants infected with *Verticillium* wilt.

Uniformity (Unif). Means the uniformity of the cotton fibers. Uniformity=100×Mean Length. Typically, fibers having a number of 77 and lower have very low uniformity, 77 to 79 is low uniformity, 80 to 82 is average uniformity, 83 to 85 is high uniformity, and above 85 is very high uniformity.

Rd. Means the distribution of reflectance of cotton fibers, as a percentage reflectance. Higher percentages mean lighter fibers, while lower percentages mean darker fibers.

+b. Means the yellowness of cotton fiber, typically on a scale of 4 to 18, where higher numbers indicate more yellowness and lower numbers indicate decreasing yellowness.

DETAILED DESCRIPTION

Cotton cultivar GW-13-1409 is a *Gossypium hirsutum* L. cotton variety which has shown uniformity and stability, as described in the following Variety Description Information. It has been self-pollinated a sufficient number of generations with careful attention to uniformity of plant type. GW-13-1409 has been increased with continued observation to uniformity.

Cotton cultivar GW-13-1409 has the following morphologic and other characteristics from data taken in the Thiva region of Greece.

Table 1

Variety Description Information

Botanical name: *Gossypium hirsutum* L.
General:
Plant Habit: Conical
Mature plant height (from cotyledonary node to terminal): 105 cm to 115 cm
Stem lodging: Resistant
Fruiting branch length: Medium, 30.0 cm to 5.00 cm
Growth: Determinate
Maturity (Date of 50% open bolls): 102 days to 112 days
Leaf (upper-most, fully expanded leaf):
Type: Palmate
Pubescence: Strong
Foliage size: Medium, average length is 15.0 cm and average width is 10.0 cm
Nectaries: Present
Leaf color: Medium-green
Glands:
Leaf: Present
Bract size: Medium
Flower:
Petal color: Cream
Pollen color: Cream
Petal spot: Absent
Type of flowering: Non-clustered
Seed:
Seed Index: 10.3 g to 11.0 g
Boll:
Gin turnout: 41.5 to 43.5
Number of seeds per boll: 28 to 35
Grams seed cotton per boll: 6.0-6.2
Number of locules per boll: 4 to 5
Boll type: Open
Boll shape: Ovate
Boll type: Storm resistant
Fiber Properties:
Method (HVI or other): HVI
Length (inches, 2.5% SL): 1.20 to 1.26
Uniformity: 87%
Strength (g/tex): 31.0
Elongation: 7.5%
Micronaire: 4.2

2014 Trials

In 2014, GW-13-1409 was tested in the two locations in Thiva and in one location in the Larissa region of Greece against the commercial cotton cultivars, (*Gossypium hirsutum*) ST-402, DP-419, Claudia, Maxa, Diva, Fantom, and Amazona.

Tests were established based on a distance of 96 cm to 98 cm between rows. All tests were conducted as four replications and randomly located. Each variety had four rows per 10 meters per replication. The distance between each plant was 20 cm. Sowing was by manual sowing machine and picking two middle rows by hand. In the Thiva trials, irrigation was by boom and in the Larissa trial irrigation was by drip. A N15, P15, and K15-type fertilizer was applied on mid-May at a rate of 30 kg/str. A urea type fertilizer was applied on mid-June 2014 at a rate of 30 kg/str and a third urea type fertilizer was applied on mid-July 2014 at a rate of 20 kg/str. A cotorane-type pesticide was applied on mid-May 2014.

Sampling began one to two days before first picking (when approximately 65% to 80% of the bolls are open, with a second picking from each variety and each of the four replications). 25 bolls were picked from the two middle rows of each replication that were chosen, and 100 bolls were randomly selected per variety. Only mature open bolls were selected. Pick was by hand and each variety was weighed separately.

In Tables 2 and 3, data from a first trial in 2014 in Thiva, Greece is shown. In Table 2, column one shows the variety name, column two shows total yield in (kg/str), column three shows total lint yield in (kg/str), column four shows the gin turnout of each variety, column five shows the weight of an individual boll in grams, column six shows the weight of 100 seeds, and column seven shows the number of seeds per boll. In Table 3, column one shows the variety name, column two shows the total bolls per plant, column three shows the percentage of open bolls, column four shows the first boll open date (days after germination), column five shows the wilt percentage, column six shows the length of fiber, column seven shows the strength of fiber, and column eight shows the micronaire of fiber. The LSD (1) compares the mean of particular variety with the grand mean of the treatments. In all tables, values that are significantly different from the mean of treatments are shown in bolded cells. LSD (2) compares mean difference between any two varieties. DAG* is days after germination.

TABLE 2

Thiva Trial No. 1 (2014)

| Variety | Yield (kg/str) 12 Oct. 2014 | Lint yield (kg/str) | GTO (%) | Weight of boll (g) | 100 Seeds weight (g) | No. of seeds per boll |
|---|---|---|---|---|---|---|
| GW-13-1145 | 510.8 | 219.2 | 42.9 | 5.7 | 10.2 | 32.2 |
| GW-11-2345 | 503.8 | 215.5 | 42.8 | 5.8 | 10.4 | 32.4 |
| GW-13-1409 | 479.0 | 200.9 | 42.0 | 5.8 | 10.8 | 31.2 |
| GW-13-921 | 472.6 | 193.8 | 41.0 | 7.0 | 13.3 | 30.7 |
| ST - 402 | 468.1 | 193.4 | 41.3 | 5.8 | 10.5 | 32.2 |
| GW-11-817 | 461.7 | 200.3 | 43.4 | 6.3 | 11.0 | 33.0 |
| GW - 2583 | 461.7 | 206.1 | 44.7 | 5.6 | 10.0 | 30.8 |
| DP - 419 | 461.1 | 187.4 | 40.6 | 6.7 | 11.5 | 34.5 |
| GW-13-985 | 455.4 | 192.8 | 42.3 | 6.5 | 12.1 | 30.4 |
| GW-11-2357 | 454.7 | 206.7 | 45.4 | 6.6 | 11.9 | 31.2 |
| CLAUDIA | 451.5 | 203.9 | 45.2 | 6.5 | 9.8 | 36.0 |
| GW - 4165 | 451.5 | 197.9 | 43.8 | 5.7 | 10.4 | 32.1 |
| FANTOM | 445.8 | 175.6 | 39.4 | 5.9 | 10.2 | 34.1 |
| GW-13-4465 | 438.8 | 181.8 | 41.4 | 6.2 | 11.9 | 29.8 |
| AMAZONA | 436.6 | 173.3 | 39.7 | 6.7 | 11.6 | 34.2 |
| DIVA | 415.2 | 174.5 | 42.0 | 6.9 | 12.1 | 33.1 |
| MAXA | 394.8 | 167.5 | 42.4 | 7.4 | 12.2 | 34.5 |
| AVERAGE | 456.7 | 193.6 | 42.4 | 6.3 | 11.2 | 32.5 |
| LSD 05 (1) | 19.5 | 10.0 | 1.1 | 0.3 | 0.6 | 1.2 |
| LSD 05 (2) | 27.6 | 14.2 | 1.5 | 0.3 | 0.9 | 1.6 |

TABLE 3

Thiva Trial No. 1 (2014)

| Variety | Boll (total) 2 Oct. 2014 | Boll open (%) 2 Oct. 2014 | First boll open-DAG* | Wilt (%) | Len | Str | Mic |
|---|---|---|---|---|---|---|---|
| GW-13-1145 | 19.1 | 97.7 | 102.0 | 3.3 | 29.5 | 30.3 | 4.5 |
| GW-11-2345 | 18.9 | 98.1 | 104.5 | 3.0 | 30.1 | 31.0 | 4.3 |
| GW-13-1409 | 20.1 | 97.6 | 105.0 | 4.0 | 30.4 | 31.2 | 4.1 |
| GW-13-921 | 16.1 | 96.7 | 106.5 | 2.5 | 30.6 | 31.3 | 4.6 |
| ST - 402 | 18.3 | 95.1 | 113.0 | 14.3 | 29.0 | 30.3 | 5.0 |
| GW-11-817 | 16.8 | 96.6 | 107.5 | 8.5 | 29.0 | 30.4 | 4.7 |
| GW - 2583 | 19.2 | 92.6 | 112.5 | 11.8 | 28.6 | 29.8 | 4.9 |
| DP - 419 | 16.9 | 90.9 | 115.0 | 16.0 | 29.1 | 29.7 | 4.5 |
| GW-13-985 | 16.3 | 94.5 | 107.0 | 2.3 | 30.1 | 30.8 | 4.4 |
| GW-11-2357 | 18.3 | 90.9 | 110.0 | 4.0 | 28.9 | 29.9 | 4.7 |
| CLAUDIA | 15.9 | 91.1 | 114.5 | 23.3 | 30.8 | 31.4 | 4.8 |
| GW - 4165 | 19.0 | 92.0 | 112.5 | 10.8 | 28.5 | 30.1 | 4.8 |
| FANTOM | 15.3 | 95.3 | 102.5 | 14.5 | 28.8 | 30.0 | 3.8 |
| GW-13-4465 | 16.5 | 94.9 | 109.0 | 3.0 | 30.8 | 31.2 | 4.1 |
| AMAZONA | 17.0 | 94.9 | 106.5 | 4.3 | 29.8 | 30.9 | 4.4 |
| DIVA | 12.6 | 97.4 | 112.5 | 8.0 | 29.0 | 31.9 | 4.3 |
| MAXA | 13.2 | 88.8 | 114.0 | 1.5 | 29.0 | 29.9 | 4.1 |
| AVERAGE | 17.0 | 94.4 | 109.1 | 7.9 | 29.5 | 30.6 | 4.5 |
| LSD 05 (1) | 1.6 | 2.4 | 2.6 | 4.2 | 0.5 | 0.5 | 0.2 |
| LSD 05 (2) | 2.3 | 3.3 | 3.6 | 5.9 | 0.8 | 0.8 | 0.3 |

In Tables 4 and 5, data from a second trial in 2014 in Thiva, Greece is shown. In Table 4, column one shows the variety name, column two shows total yield in (kg/str), column three shows total lint yield in (kg/str), column four shows the gin turnout of each variety, column five shows the weight of an individual boll in grams, column six shows the weight of 100 seeds, and column seven shows the number of seeds per boll. In Table 5, column one shows the variety name, column two shows the total bolls per plant, column three shows the percentage of open bolls, column four shows the first boll open date (days after germination), column five shows the wilt percentage, column six shows the length of the fiber, column seven shows the strength of the fiber, and column eight shows the micronaire of the fiber.

TABLE 4

Thiva Trial No. 2 (2014)

| Variety | Yield (kg/str) 14 Oct. 2014 | Lint yield (kg/str) | GTO (%) | Weight of boll (g) | 100 seed weight (g) | No. of seeds per boll |
|---|---|---|---|---|---|---|
| GW-11-2345 | 456.6 | 193.2 | 42.3 | 5.4 | 10.2 | 30.6 |
| GW-13-1409 | 436.9 | 187.0 | 42.8 | 5.5 | 10.3 | 30.0 |
| GW-13-1145 | 431.1 | 182.3 | 42.3 | 5.4 | 10.0 | 31.2 |
| ST - 402 | 424.1 | 171.6 | 40.5 | 5.5 | 10.9 | 30.0 |
| GW - 2583 | 398.0 | 174.9 | 44.0 | 5.3 | 10.0 | 29.4 |
| AMAZONA | 394.8 | 156.0 | 39.5 | 6.2 | 11.3 | 32.8 |
| GW - 4165 | 394.1 | 169.4 | 43.0 | 5.4 | 10.3 | 29.7 |
| DP - 419 | 387.8 | 157.3 | 40.5 | 6.3 | 11.5 | 32.8 |
| GW-11-2357 | 379.5 | 173.1 | 45.6 | 6.3 | 11.4 | 30.0 |
| GW-11-817 | 371.2 | 157.4 | 42.4 | 6.2 | 10.5 | 33.2 |
| GW-13-985 | 360.3 | 155.4 | 43.1 | 5.9 | 11.2 | 29.6 |
| GW-13-4465 | 356.5 | 146.5 | 41.1 | 5.7 | 11.6 | 28.6 |
| GW-13-921 | 352.7 | 144.4 | 40.9 | 6.5 | 12.3 | 30.8 |
| FANTOM | 349.5 | 133.7 | 38.2 | 5.6 | 10.5 | 32.9 |
| CLAUDIA | 331.0 | 144.5 | 43.7 | 6.1 | 9.9 | 34.6 |
| MAXA | 304.8 | 126.6 | 41.5 | 6.9 | 12.2 | 32.9 |
| DIVA | 253.2 | 101.1 | 39.9 | 6.6 | 12.2 | 31.7 |
| AVERAGE | 375.4 | 157.3 | 41.8 | 5.9 | 11.0 | 31.2 |
| LSD 05 (1) | 30.8 | 14.2 | 1.1 | 0.3 | 0.5 | 1.1 |
| LSD 05 (2) | 43.6 | 20.1 | 1.6 | 0.4 | 0.7 | 1.6 |

TABLE 5

Thiva Trial No. 2 (2014)

| Variety | Boll (total) 2 Oct. 2014 | Boll open (%) 2 Oct. 2014 | First boll open-DAG* | Wilt % | Len | Str | Mic |
|---|---|---|---|---|---|---|---|
| GW-11-2345 | 15.6 | 97.9 | 103.5 | 1.5 | 29.9 | 31.2 | 4.3 |
| GW-13-1409 | 14.9 | 96.9 | 104.5 | 3.3 | 30.6 | 31.6 | 4.1 |
| GW-13-1145 | 16.9 | 94.2 | 101.0 | 2.0 | 28.9 | 30.0 | 4.5 |
| ST - 402 | 18.3 | 87.1 | 112.5 | 8.0 | 29.1 | 30.2 | 5.1 |
| GW - 2583 | 17.1 | 86.5 | 111.5 | 8.5 | 28.5 | 30.0 | 5.0 |
| AMAZONA | 14.9 | 90.5 | 106.0 | 5.5 | 29.1 | 30.0 | 4.4 |
| GW - 4165 | 17.2 | 80.1 | 112.5 | 7.0 | 28.5 | 30.0 | 5.0 |
| DP - 419 | 15.8 | 85.7 | 114.0 | 12.5 | 28.4 | 29.3 | 4.9 |
| GW-11-2357 | 14.8 | 88.9 | 106.0 | 6.5 | 28.7 | 29.5 | 4.7 |
| GW-11-817 | 15.7 | 93.8 | 106.5 | 7.8 | 29.4 | 30.7 | 4.8 |
| GW-13-985 | 14.4 | 95.9 | 105.5 | 1.5 | 29.6 | 30.5 | 4.5 |
| GW-13-4465 | 13.0 | 96.6 | 107.5 | 4.5 | 30.2 | 30.9 | 4.0 |
| GW-13-921 | 12.0 | 93.2 | 105.5 | 1.0 | 30.2 | 30.9 | 4.6 |
| FANTOM | 13.7 | 90.9 | 101.5 | 16.8 | 28.7 | 30.2 | 4.0 |
| CLAUDIA | 14.1 | 71.8 | 114.5 | 6.5 | 30.3 | 31.6 | 4.7 |
| MAXA | 9.9 | 89.4 | 114.0 | 4.8 | 29.4 | 31.2 | 4.2 |
| DIVA | 12.0 | 83.3 | 113.0 | 4.3 | 29.0 | 31.7 | 4.1 |
| AVERAGE | 14.7 | 89.6 | 108.2 | 6.0 | 29.3 | 30.5 | 4.5 |
| LSD 05 (1) | 1.5 | 5.4 | 2.7 | 2.6 | 0.5 | 0.6 | 0.2 |
| LSD 05 (2) | 2.2 | 7.6 | 3.9 | 3.6 | 0.6 | 0.8 | 0.3 |

In Tables 6 and 7, data from a trial in 2014 in Larissa, Greece is shown. In Table 6, column one shows the variety name, column two shows total yield in (kg/str), column three shows total lint yield in (kg/str), column four shows the gin turnout of each variety, column five shows the weight of an individual boll in grams, and column six shows the weight of 100 seeds. In Table 7, column one shows the variety name, column two shows the number of seeds per boll, column three shows the total bolls per plant, column four shows the percentage of open bolls on the date, column five shows the length of the fiber, column six shows the strength of the fiber, and column seven shows the micronaire of the fiber.

TABLE 6

Larissa Trial (2014)

| Variety | Yield (kg/str) 22 Oct. 2014 | Lint yield (kg/str) | GTO (%) | Weight of boll (g) | 100 seeds weight (g) |
|---|---|---|---|---|---|
| GW-13-1409 | 428.6 | 189.3 | 44.2 | 5.6 | 10.2 |
| GW-4165 | 413.3 | 186.3 | 45.0 | 5.3 | 9.8 |
| GW-11-2345 | 403.1 | 180.2 | 44.7 | 5.2 | 9.5 |
| ST-402 | 400.8 | 168.2 | 42.0 | 5.5 | 10.2 |
| GW-2583 | 400.5 | 181.7 | 45.3 | 5.3 | 9.8 |
| GW-13-1145 | 391.1 | 171.4 | 43.9 | 5.6 | 10.1 |
| DP-419 | 372.4 | 157.1 | 42.2 | 6.4 | 10.9 |
| GW-13-921 | 366.1 | 157.0 | 42.9 | 6.5 | 12.4 |
| AMAZONA | 353.8 | 149.3 | 42.2 | 6.0 | 10.6 |
| GW-13-985 | 352.0 | 155.3 | 44.1 | 5.8 | 11.3 |
| CLAUDIA | 343.6 | 157.3 | 45.8 | 6.1 | 9.6 |
| GW-11-817 | 340.0 | 150.2 | 44.2 | 5.8 | 10.4 |
| GW-11-2357 | 278.8 | 132.3 | 47.5 | 5.9 | 10.7 |
| FANTOM | 268.6 | 108.0 | 40.2 | 5.5 | 9.9 |
| GW-13-4465 | 256.4 | 108.1 | 42.2 | 5.6 | 11.3 |
| MAXA | 239.8 | 106.5 | 44.4 | 6.7 | 11.8 |
| DIVA | 234.7 | 101.3 | 43.2 | 6.7 | 11.8 |
| AVERAGE | 343.7 | 150.6 | 43.8 | 5.9 | 10.6 |
| LSD 05 (1) | 39.3 | 18.0 | 1.0 | 0.3 | 0.5 |
| LSD 05 (2) | 55.5 | 25.4 | 1.5 | 0.5 | 0.8 |

TABLE 7

Larissa Trial (2014)

| Variety | No. of seeds per boll | Boll (total) 21 Sep. 2014 | Boll open (%) 21 Sep. 2014 | Len | Str | Mic |
|---|---|---|---|---|---|---|
| GW-13-1409 | 31.0 | 17.5 | 81.5 | 30.0 | 30.8 | 4.0 |
| GW - 4165 | 30.1 | 15.2 | 74.6 | 28.5 | 30.0 | 4.8 |
| GW-11-2345 | 30.5 | 16.2 | 88.2 | 30.2 | 30.5 | 4.0 |
| ST - 402 | 30.5 | 15.6 | 72.7 | 28.9 | 30.3 | 5.2 |
| GW - 2583 | 29.3 | 16.7 | 73.3 | 28.9 | 30.2 | 4.8 |
| GW-13-1145 | 31.0 | 15.3 | 92.0 | 29.6 | 30.2 | 4.3 |
| DP - 419 | 33.4 | 17.4 | 65.4 | 28.5 | 29.9 | 4.5 |
| GW-13-921 | 30.0 | 13.8 | 84.6 | 29.5 | 31.0 | 4.7 |
| AMAZONA | 32.3 | 12.7 | 92.4 | 29.2 | 30.5 | 4.3 |
| GW-13-985 | 28.8 | 14.5 | 89.4 | 30.2 | 31.0 | 4.3 |
| CLAUDIA | 34.6 | 13.9 | 65.7 | 30.2 | 31.6 | 4.5 |
| GW-11-817 | 30.9 | 12.3 | 87.5 | 29.3 | 29.9 | 4.8 |
| GW-11-2357 | 28.8 | 14.2 | 88.2 | 28.7 | 29.9 | 4.7 |
| FANTOM | 32.8 | 12.8 | 89.1 | 29.0 | 29.5 | 3.8 |
| GW-13-4465 | 28.7 | 13.4 | 84.5 | 30.3 | 31.1 | 3.9 |
| MAXA | 31.3 | 10.5 | 71.1 | 29.0 | 29.8 | 4.0 |
| DIVA | 32.5 | 10.9 | 66.9 | 28.7 | 30.4 | 4.2 |
| AVERAGE | 31.0 | 14.3 | 80.4 | 29.3 | 30.4 | 4.4 |
| LSD 05 (1) | 1.2 | 1.7 | 7.1 | 0.4 | 0.6 | 0.2 |
| LSD 05 (2) | 1.7 | 2.4 | 10.1 | 0.6 | 0.8 | 0.3 |

2015 Trials

In 2015, GW-13-1409 was tested in two locations in Thiva, Greece against the commercial cotton cultivars (Gossypium hirsutum) ST-402, DP-332, Celia, Fantom, Lider, and Elpida. The performance characteristics of cotton cultivar GW-13-1409 and the comparison cultivars were analyzed, and results are shown in Tables 8-13.

Tests were established based on a distance between rows of 96-98 cm. All tests had four replications and were randomly located. Each variety had four rows per 10 meters per replication. The distance between each plant was 20 cm. Sowing was by manual sowing machine and picking two middle rows by hand. In all trial locations, irrigation was by boom. A N15, P15, and K15 type fertilizer was applied on mid-May at a rate of 30 kg/str. A urea type fertilizer was applied on mid-June 2015 at a rate of 30 kg/str and a third urea type fertilizer was applied on mid-July 2015 at a rate of 20 kg/str. A cotorane type pesticide was applied on mid-May 2015.

Sampling began one to two days before first picking (when approximately 65% to 80% of the bolls are open, with a second picking from each variety and each of the four replications). 25 bolls were picked from the two middle rows of each replication that were chosen, and 100 bolls were randomly selected per variety. Only mature open bolls were selected. Pick was by hand and each variety was weighed separately.

Tables 8-10 show the first trial in 2015 in Thiva, Greece. In Table 8, the first column shows the variety name, the second column shows total yield in (kg/str), column three shows total lint yield in (kg/str), column four shows the gin turnout of each variety, column five shows the weight of an individual boll, and column six shows the weight of 100 seeds. In Table 9, the first column shows the variety name, column two shows the number of seeds per boll, column three shows the total bolls per plant, column four shows the percentage of open bolls on the date, and column five shows the first boll open date (days after germination). In Table 10, the first column shows the variety name, column two shows the length of the fiber, column three shows the strength of the fiber, column four shows the micronaire of the fiber, column five shows the uniformity of the fiber, column six shows the elongation of the fiber, column seven shows the distribution of reflectance of the fiber, and column eight shows the yellowness of the fiber.

TABLE 8

Thiva Trial No. 1 (2015)

| Variety | Yield (kg/str) 16 Oct. 2015 | Lint yield (kg/str) | GTO (%) | Weight of boll (g) | 100 Seeds weight (g) |
|---|---|---|---|---|---|
| ELPIDA | 422.2 | 173.9 | 41.2 | 6.0 | 11.5 |
| GW-14-1025 | 417.1 | 175.9 | 42.2 | 6.2 | 11.1 |
| GW-13-3679 | 411.3 | 171.6 | 41.7 | 5.7 | 10.9 |
| GW-13-1409 | 399.2 | 165.4 | 41.4 | 6.2 | 11.5 |
| FANTOM | 396.0 | 150.2 | 37.9 | 6.1 | 11.2 |
| GW-14 1073 | 390.9 | 165.1 | 42.2 | 6.1 | 12.2 |
| GW-13-921 | 371.2 | 147.9 | 39.9 | 6.4 | 13.2 |
| GW-14-2153 | 371.2 | 154.8 | 41.7 | 6.6 | 11.5 |
| GW-14-625 | 361.0 | 150.7 | 41.8 | 6.0 | 11.8 |
| GW-14-4753 | 337.4 | 134.3 | 39.8 | 6.2 | 11.9 |
| ST-402 | 336.7 | 131.0 | 38.9 | 5.7 | 11.3 |
| GW-13-3681 | 330.4 | 139.0 | 42.0 | 6.4 | 11.0 |
| GW-2583 | 314.4 | 133.8 | 42.7 | 5.8 | 10.9 |
| CELIA | 311.2 | 125.0 | 40.2 | 7.0 | 12.3 |
| LIDER | 307.4 | 127.3 | 41.3 | 5.7 | 10.8 |
| DP-332 | 301.0 | 124.8 | 41.5 | 5.9 | 10.8 |
| AVERAGE | 361.2 | 148.2 | 41.0 | 6.1 | 11.5 |
| LSD 05 (1) | 28.0 | 12.4 | 1.0 | 0.2 | 0.4 |
| LSD 05 (2) | 39.6 | 17.5 | 1.5 | 0.3 | 0.6 |

TABLE 9

Thiva Trial No. 1 (2015)

| Variety | No. of seeds per boll | Boll (total) 20 Sep. 2015 | Boll open (%) 20 Sep. 2015 | First boll open (DAG*) |
|---|---|---|---|---|
| ELPIDA | 30.3 | 10.4 | 66.8 | 103.5 |
| GW-14-1025 | 32.5 | 10.4 | 63.4 | 105.5 |
| GW-13-3679 | 29.1 | 11.1 | 69.6 | 101.3 |
| GW-13-1409 | 31.0 | 12.6 | 44.6 | 102.8 |
| FANTOM | 33.9 | 10.1 | 64.7 | 102.5 |
| GW-14 1073 | 28.9 | 10.7 | 70.1 | 104.5 |
| GW-13-921 | 28.8 | 11.1 | 57.6 | 103.0 |
| GW-14-2153 | 33.6 | 9.2 | 52.9 | 105.0 |
| GW-14-625 | 28.9 | 9.1 | 62.8 | 105.0 |
| GW-14-4753 | 30.9 | 9.1 | 52.8 | 106.5 |
| ST-402 | 30.7 | 10.3 | 19.7 | 110.5 |
| GW-13-3681 | 33.5 | 9.7 | 30.1 | 107.5 |
| GW-2583 | 31.1 | 10.9 | 22.4 | 112.0 |
| CELIA | 33.9 | 8.7 | 28.1 | 111.0 |
| LIDER | 30.6 | 11.0 | 21.9 | 112.0 |
| DP-332 | 31.7 | 10.7 | 21.8 | 112.5 |
| AVERAGE | 31.2 | 10.3 | 46.8 | 106.6 |
| LSD 05 (1) | 1.2 | 1.0 | 12.6 | 2.4 |
| LSD 05 (2) | 1.7 | 1.4 | 17.8 | 3.4 |

TABLE 10

Thiva Trial No. 1 (2015)

| Variety | LEN | STR | Mic | Unif | Elons | Rd | +b |
|---|---|---|---|---|---|---|---|
| ELPIDA | 31.6 | 31.0 | 4.4 | 87.2 | 7.1 | 82.2 | 8.5 |
| GW-14-1025 | 31.0 | 31.2 | 4.6 | 86.3 | 7.1 | 83.1 | 8.2 |
| GW-13-3679 | 32.2 | 31.4 | 4.3 | 86.3 | 7.9 | 83.0 | 8.5 |
| GW-13-1409 | 32.1 | 30.9 | 4.2 | 86.3 | 7.5 | 83.4 | 8.3 |
| FANTOM | 29.9 | 30.1 | 4.0 | 86.2 | 7.6 | 83.9 | 8.4 |
| GW-14 1073 | 30.4 | 31.1 | 4.4 | 85.3 | 6.6 | 82.4 | 8.3 |
| GW-13-921 | 31.8 | 32.0 | 4.5 | 86.1 | 6.9 | 83.6 | 8.3 |
| GW-14-2153 | 31.9 | 31.3 | 4.4 | 86.8 | 7.4 | 81.9 | 8.5 |
| GW-14-625 | 30.7 | 30.8 | 4.5 | 86.4 | 7.1 | 82.9 | 8.3 |
| GW-14-4753 | 31.9 | 30.9 | 4.1 | 87.5 | 6.7 | 86.5 | 7.7 |
| ST-402 | 31.2 | 31.8 | 4.8 | 88.1 | 6.6 | 81.0 | 8.6 |
| GW-13-3681 | 28.7 | 29.8 | 4.4 | 86.1 | 6.9 | 83.5 | 8.0 |
| GW - 2583 | 28.9 | 31.2 | 4.8 | 87.0 | 7.2 | 80.8 | 8.8 |
| CELIA | 30.3 | 33.3 | 4.5 | 87.3 | 5.6 | 84.5 | 7.9 |
| LIDER | 28.9 | 31.8 | 4.9 | 86.5 | 7.1 | 80.1 | 9.1 |
| DP-332 | 29.9 | 33.0 | 4.6 | 87.1 | 6.6 | 80.9 | 8.7 |
| AVERAGE | 30.7 | 31.3 | 4.5 | 86.6 | 7.0 | 82.7 | 8.4 |
| LSD 05 (1) | 0.8 | 0.8 | 0.2 | 0.8 | 0.4 | 1.1 | 0.3 |
| LSD 05 (2) | 1.1 | 1.1 | 0.2 | 1.1 | 0.6 | 1.6 | 0.4 |

TABLE 11

THIVA TRIAL NO. 2 (2015)

| Variety | Yield (kg/str) 13 Oct. 2015 | Lint yield (kg/str) | GTO (%) | Weight of boll (g) | 100 Seeds weight (g) |
|---|---|---|---|---|---|
| GW-13-3679 | 448.3 | 190.1 | 42.4 | 6.0 | 11.2 |
| GW-13-1409 | 442.0 | 185.2 | 41.9 | 6.2 | 10.8 |
| GW-14-1025 | 433.0 | 185.3 | 42.8 | 6.6 | 11.6 |
| ELPIDA | 429.2 | 178.7 | 41.6 | 6.2 | 11.6 |
| GW-14-2153 | 425.4 | 177.6 | 42.0 | 7.0 | 11.5 |
| FANTOM | 415.2 | 153.8 | 37.0 | 6.5 | 11.4 |
| GW-14 1073 | 413.3 | 173.4 | 42.0 | 6.6 | 12.6 |
| GW-13-921 | 408.2 | 162.1 | 39.7 | 7.0 | 13.7 |
| GW-14-625 | 405.0 | 170.0 | 42.0 | 6.5 | 12.5 |
| GW-13-3681 | 403.1 | 174.8 | 43.4 | 6.8 | 11.1 |
| CELIA | 384.6 | 156.2 | 40.6 | 7.2 | 12.8 |
| ST-402 | 378.2 | 151.2 | 39.9 | 6.0 | 11.4 |
| GW-14-4753 | 368.6 | 149.8 | 40.6 | 6.5 | 12.1 |
| LIDER | 366.7 | 151.1 | 41.2 | 6.0 | 11.2 |
| GW-2583 | 361.6 | 149.4 | 41.3 | 6.1 | 11.3 |
| DP-332 | 329.7 | 139.0 | 42.1 | 6.1 | 10.9 |
| AVERAGE | 400.7 | 165.5 | 41.3 | 6.5 | 11.7 |
| LSD 05 (1) | 22.5 | 10.6 | 1.0 | 0.2 | 0.5 |
| LSD 05 (2) | 31.8 | 15.1 | 1.4 | 0.3 | 0.7 |

TABLE 12

THIVA TRIAL NO. 2 (2015)

| Variety | No. of seeds per boll | Boll (total) 19 Sep. 2015 | Boll open (%) 19 Sep. 2015 | First boll open-DAG* |
|---|---|---|---|---|
| GW-13-3679 | 31.5 | 16.3 | 75.3 | 100.0 |
| GW-13-1409 | 32.5 | 15.4 | 68.6 | 102.0 |
| GW-14-1025 | 33.4 | 15.2 | 64.4 | 104.5 |
| ELPIDA | 31.0 | 15.3 | 74.6 | 101.3 |
| GW-14-2153 | 34.8 | 13.3 | 63.6 | 105.5 |
| FANTOM | 35.6 | 14.0 | 73.2 | 103.5 |
| GW-14 1073 | 30.3 | 14.0 | 68.3 | 105.3 |
| GW-13-921 | 30.5 | 13.1 | 63.4 | 105.0 |
| GW-14-625 | 29.9 | 13.5 | 70.8 | 104.3 |
| GW-13-3681 | 34.7 | 14.5 | 53.5 | 106.8 |
| CELIA | 33.4 | 11.9 | 47.5 | 111.5 |
| ST-402 | 31.8 | 16.0 | 40.4 | 109.3 |
| GW-14-4753 | 31.9 | 14.9 | 66.9 | 106.0 |
| LIDER | 31.3 | 13.3 | 38.0 | 110.5 |
| GW-2583 | 32.0 | 13.3 | 39.9 | 110.0 |
| DP-332 | 32.2 | 14.7 | 40.3 | 109.0 |
| AVERAGE | 32.3 | 14.3 | 59.3 | 105.9 |
| LSD 05 (1) | 1.0 | 1.2 | 9.6 | 2.1 |
| LSD 05 (2) | 1.5 | 1.6 | 13.6 | 3.0 |

Tables 11-13 show the second trial in 2015 in Thiva, Greece. In Table 11, the first column shows the variety name, the second column shows total yield in (kg/str), column three shows total lint yield in (kg/str), column four shows the gin turnout of each variety, column five shows the weight of an individual boll, and column six shows the weight of 100 seeds. In Table 12, the first column shows the variety name, column two shows the number of seeds per boll, column three shows the total bolls per plant, column four shows the percentage of open bolls on the date, and column five shows the first boll open date (days after germination). In Table 13, the first column shows the variety name, column two shows the length of the fiber, column three shows the strength of the fiber, column four shows the micronaire of the fiber, column five shows the uniformity of the fiber, column six shows the elongation of the fiber, column seven shows the distribution of reflectance of the fiber, and column eight shows the yellowness of the fiber.

TABLE 13

THIVA TRIAL NO. 2 (2015)

| Variety | Len | Str | Mic | Unif | Elong | Rd | +b |
|---|---|---|---|---|---|---|---|
| GW-13-3679 | 32.1 | 31.5 | 4.3 | 87.8 | 7.8 | 82.7 | 8.3 |
| GW-13-1409 | 31.9 | 30.6 | 4.2 | 87.0 | 7.0 | 83.3 | 8.4 |
| GW-14-1025 | 30.8 | 30.5 | 4.5 | 87.4 | 6.8 | 83.0 | 8.4 |
| ELPIDA | 31.7 | 31.1 | 4.5 | 86.2 | 7.4 | 83.0 | 8.3 |
| GW-14-2153 | 32.2 | 31.4 | 4.5 | 86.8 | 7.8 | 79.6 | 8.8 |
| FANTOM | 29.8 | 30.5 | 3.8 | 86.4 | 7.1 | 83.0 | 8.5 |
| GW-14 1073 | 30.5 | 31.3 | 4.7 | 85.5 | 6.2 | 82.0 | 8.5 |
| GW-13-921 | 31.5 | 31.2 | 4.5 | 88.1 | 6.9 | 83.1 | 8.2 |
| GW-14-625 | 30.7 | 30.1 | 4.5 | 87.3 | 7.0 | 83.4 | 8.5 |
| GW-13-3681 | 28.4 | 29.6 | 4.3 | 85.8 | 6.5 | 84.0 | 8.3 |
| CELIA | 30.3 | 32.6 | 4.3 | 86.1 | 5.2 | 84.2 | 8.1 |
| ST-402 | 30.4 | 30.2 | 4.7 | 86.3 | 6.2 | 81.4 | 8.7 |
| GW-14-4753 | 31.6 | 30.5 | 4.0 | 87.4 | 6.9 | 85.0 | 8.0 |
| LIDER | 30.4 | 32.5 | 4.7 | 86.9 | 7.0 | 79.9 | 8.9 |
| GW - 2583 | 30.1 | 32.2 | 4.5 | 86.7 | 6.5 | 81.3 | 8.8 |
| DP-332 | 29.8 | 32.0 | 4.6 | 86.4 | 7.3 | 81.2 | 8.6 |

TABLE 13-continued

THIVA TRIAL NO. 2 (2015)

| Variety   | Len  | Str  | Mic | Unif | Elong | Rd   | +b  |
|-----------|------|------|-----|------|-------|------|-----|
| AVERAGE   | 30.7 | 31.1 | 4.4 | 86.7 | 6.8   | 82.5 | 8.5 |
| LSD 05 (1)| 0.7  | 0.7  | 0.2 | 0.7  | 0.5   | 1.2  | 0.2 |
| LSD 05 (2)| 1.0  | 1.0  | 0.2 | 1.0  | 0.7   | 1.6  | 0.3 |

Further Embodiments

One embodiment is related to methods for crossing the cotton variety GW-13-1409 with itself or a second plant and the seeds and plants produced by such methods. These methods can be used for propagation of the cotton variety GW-13-1409, or can be used to produce hybrid cotton seeds and the plants grown therefrom. A hybrid plant can be used as a recurrent parent at any given stage in a backcrossing protocol during the production of a single locus conversion of the cotton variety GW-13-1409.

GW-13-1409 is well-suited to the development of new varieties based on the elite nature of the genetic background of the variety. In selecting a second plant to cross with GW-13-1409 for the purpose of developing novel cotton varieties, it will typically be desired to choose those plants which themselves exhibit one or more selected desirable characteristics. Examples of potentially desired characteristics include higher fiber (lint) yield, earlier maturity, improved fiber quality, resistance to diseases and insects, tolerance to drought and heat, and improved agronomic traits.

When cotton variety GW-13-1409 is crossed with another, different, variety, first generation, $F_1$, cotton progeny are produced. The hybrid progeny are produced regardless of characteristics of the two varieties produced. As such, an $F_1$ hybrid cotton plant may be produced by crossing GW-13-1409 with any second cotton plant. The second cotton plant may be genetically homogeneous (e.g., inbred) or may itself be a hybrid. Therefore, any $F_1$ hybrid cotton plant produced by crossing cotton variety GW-13-1409 with a second cotton plant is a part of the embodiments.

Cotton plants can be crossed by either natural or mechanical techniques. Natural pollination occurs in cotton either by self-pollination or natural cross pollination, which typically is aided by pollinating organisms. In either natural or artificial crosses, flowering and flowering time are important considerations.

Cotton Biology

The cotton flower is perfect in that the male and female structures are in the same flower. The crossed or hybrid seed can be produced by manual crosses between selected parents. Floral buds of the parent that is to be the female can be emasculated prior to the opening of the flower by manual removal of the male anthers. At flowering, the pollen from flowers of the parent plants designated as male, can be manually placed on the stigma of the previous emasculated flower. Seed developed from the cross is known as first generation $F_1$ hybrid seed. Planting of this seed produces $F_1$ plants of which half their genetic component is from the female parent and half from the male parent. Segregation of genes begins at meiosis thus producing second generation $F_2$ seed. Assuming multiple genetic differences between the original parents, each $F_2$ seed has a unique combination of genes.

Self-pollination occurs naturally in cotton with no manipulation of the flowers. For the crossing of two cotton plants, it may be beneficial to use artificial hybridization. In artificial hybridization, the flower used as a female in a cross is manually cross pollinated prior to maturation of pollen from the flower, thereby preventing self-fertilization, or alternatively, the male parts of the flower are emasculated using a technique known in the art. Techniques for emasculating the male parts of a cotton flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and could develop into flowers at a later date. The flower is grasped between the thumb and index finger and the location of the stigma determined by examining the sepals. The calyx is removed by grasping a sepal with the forceps, pulling it down and around the flower, and repeating the procedure until the five sepals are removed. The exposed corolla is removed with care to avoid injuring the stigma. Cross-pollination can then be carried out using, for example, petri dishes or envelopes in which male flowers have been collected. Desiccators containing calcium chloride crystals can be used in some environments to dry male flowers to obtain adequate pollen shed.

Either with or without emasculation of the female flower, hand pollination can be carried out by removing the stamens and pistil with forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Cross-pollination is more common within rows than between adjacent rows; therefore, it may be beneficial to grow populations with genetic male sterility on a square grid to create rows in all directions. For example, single-plant hills on 50-cm centers may be used, with subdivision of the area into blocks of an equal number of hills for harvest from bulks of an equal amount of seed from male-sterile plants in each block to enhance random pollination.

The two cotton species commercially grown in the United States are *Gossypium hirsutum*, commonly known as short staple or upland cotton and *Gossypium barbadense*, commonly known as extra long staple (ELS) or, in the United States, as Pima cotton. Upland cotton fiber is used in a wide array of coarser spin count products. Pima cotton is used in finer spin count yarns (50-80) which are primarily used in more expensive garments. Other properties of Pima cotton are critical because of fiber end use.

Cotton is an important and valuable field crop. Thus, a continuing goal of plant breeders is to develop stable, high yielding cotton varieties that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include resistance to diseases and insects, tolerance to drought and heat, tolerance to herbicides, improvements in fiber traits and numerous other agronomic traits that may be desirable to the farmer or end user.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable variety. This approach has been used extensively for breeding disease-resistant plant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial varieties. Those still deficient in a few traits may be used as parents to produce new populations for further selection.

These processes, which lead to the final step of marketing and distribution, may take as much as eight to 12 years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value may be masked by other confounding plant traits or environmental factors. One method of identifying a superior plant is to observe its performance relative to other experimental plants and to one or more widely grown standard varieties. Single observations are generally inconclusive, while replicated observations provide a better estimate of genetic worth.

The goal of plant breeding is to develop new, unique and superior cotton varieties. The breeder initially selects and crosses two or more parental lines, followed by repeated selfing and selection, producing many new genetic combinations. Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large amounts of research monies to develop superior new cotton varieties.

Pureline cultivars, such as generally used in cotton and many other crops, are commonly bred by hybridization of two or more parents followed by selection. The complexity of inheritance, the breeding objectives and the available resources influence the breeding method. The development of new varieties requires development and selection, the crossing of varieties and selection of progeny from superior crosses.

Single Gene Conversion and Backcrossing

The term single gene converted plant as used herein refers to those cotton plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental cotton plant that contributes the gene for the desired characteristic is termed the nonrecurrent or donor parent.

Another aspect provides for plants modified to include at least a first desired trait. Such plants may, in one embodiment, be developed by a plant breeding technique called backcrossing, wherein essentially all of the morphological and physiological characteristics of a variety are recovered in addition to a genetic locus transferred into the hybrid via the backcrossing technique. The term backcrossing as used herein refers to the repeated crossing of a hybrid progeny back to a starting variety into which introduction of the desired trait is being carried out. The parental plant which contributes the locus or loci for the desired trait is termed the nonrecurrent or donor parent. This terminology refers to the fact that the nonrecurrent parent is used one time in the backcross protocol and therefore does not recur.

The parental cotton plant to which the locus or loci from the nonrecurrent parent are transferred is known as the recurrent parent as it is used for several rounds in the backcrossing protocol (Poehlman and Sleper, In: Breeding Field Crops, Iowa State University Press, Ames, 1995; Sprague and Dudley, In: Corn and Improvement, 3rd ed., 1988; Fehr, In: Principles of variety development, Theory and Technique (Vol 1) and Crop Species Soybean (Vol 2), Iowa State Univ., Macmillian Pub. Co., NY, 360-376, 1987b; Fehr, In: Soybeans: Improvement, Production and Uses, 2d Ed., Monograph 16:249, 1987). In a typical backcross protocol, the original line of interest (recurrent parent) is crossed to a second variety (nonrecurrent parent) that carries the genetic locus to be transferred. The resulting progeny from this cross are then crossed again to the recurrent parent and the process is repeated until a cotton plant is obtained wherein essentially all of the morphological and physiological characteristics of the recurrent parent are recovered in the converted plant, in addition to the transferred locus from the nonrecurrent parent.

The backcross process may be accelerated by the use of genetic markers, such as Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998) to identify plants with the greatest genetic complement from the recurrent parent.

The selection of a suitable recurrent parent is an important step for a successful backcrossing procedure. The goal of a backcross protocol is to add or substitute one or more new traits in a variety. To accomplish this, a genetic locus of the recurrent parent is modified or substituted with the desired locus from the nonrecurrent parent, while retaining essentially all of the rest of the genetic, and therefore the morphological and physiological constitution of the original variety. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide tolerance, resistance for bacterial, fungal, or viral disease, insect or nematode resistance, male sterility, ease of transformation, resistance to abiotic stresses and improved fiber characteristics. These genes are generally inherited through the nucleus, but may be inherited through the cytoplasm.

Pedigree Breeding

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes. The new varieties are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$ plants. Selection of the best individuals may begin in the $F_2$ population or later depending upon objectives of the breeder; then, beginning in the $F_3$, the best individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines are typically tested for potential release as new varieties.

Mass and Recurrent Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Single Seed-Descent

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Modified-Single Seed Descent

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population. The multiple-seed procedure may be used to save labor. It is considerably faster to gin bolls with a machine than to remove one seed by hand for the single-seed procedure. The multiple-seed procedure also makes it possible to plant the same number of seeds of a population each generation of inbreeding. Enough seeds are harvested to make up for those plants that did not germinate or produce seed.

Direct Selection

Direct selection may be applied where a genetic locus acts as a dominant trait. An example of a dominant trait is the herbicide tolerance trait. For this selection process, the progeny of the initial cross are sprayed with the herbicide prior to the backcrossing. The spraying eliminates any plants which do not have the desired herbicide tolerance characteristic, and only those plants which have the herbicide tolerance gene are used in the subsequent backcross. This process is then repeated for all additional backcross generations.

Additional Breeding Methods

Descriptions of other breeding methods that are commonly used for different traits and crops can be found in one of several reference books (e.g., Allard, In: Principles of plant breeding, John Wiley & Sons, NY, University of California, Davis, Calif., 50-98, 1960; Simmonds, In: Principles of crop improvement, Longman, Inc., NY, 369-399, 1979; Sneep and Hendriksen, In: Plant breeding perspectives, Wageningen (Ed), Center for Agricultural Publishing and Documentation, 1979; Fehr, In: Principles of variety development, Theory and Technique (Vol 1) and Crop Species Soybean (Vol 2), Iowa State Univ., Macmillian Pub. Co., NY, 360-376, 1987; Fehr, In: Soybeans: Improvement, Production and Uses, 2d Ed., Monograph 16:249, 1987). Additionally, with any of the methods disclosed above, mutagenesis can be utilized to increase the diversity of the gene pool that is available in the breeding program.

Breeding with Molecular Markers

In addition to phenotypic observations, a plant can also be characterized by its genotype. The genotype of a plant can be determined by a molecular marker profiling, which can be applied to plants of the same variety or a related variety, can reveal genetic difference of plants and plant parts which are genetically superior as a result of an event comprising a backcross conversion, transgene, or genetic sterility factor, and can be used to reveal or validate a pedigree or genetic relationship among test materials. Such molecular marker profiling can be accomplished by using a variety of techniques including, but not limited to, restriction fragment length polymorphism (RFLP), amplified fragment length polymorphism (AFLP), sequence-tagged sites (STS), randomly amplified polymorphic DNA (RAPD), arbitrarily primed polymerase chain reaction (AP-PCR), DNA amplification fingerprinting (DAF), sequence characterized amplified regions (SCARs), variable number tandem repeat (VNTR), short tandem repeat (STR), single feature polymorphism (SFP), simple sequence length polymorphism (SSLP), restriction site associated DNA, allozymes, isozyme markers, single nucleotide polymorphisms (SNPs), or simple sequence repeat (SSR) markers, also known as microsatellites (Gupta et al., 1999; Korzun et al., 2001). Various types of these marker platforms, for example, can be used to identify individual varieties developed from specific parent varieties, as well as cells, or other plant parts thereof. See, for example, Tyagi et al. (2014) "Genetic diversity and population structure in the US Upland cotton (*Gossypium hirsutum* L.)," Theoretical and Applied Genetics 127(2): 283-295; Tatineni et al. (1996) "Genetic diversity in elite cotton germplasm determined by morphological characteristics and RAPDs," Crop Science 36(1): 186-192; and Cho et al. (2014) "Genome-wide SNP marker panel applicable to Cotton Genetic diversity test," Proceedings of the International Cotton Genome Initiative Conference 2(1):11, each of which are incorporated by reference herein in their entirety.

In some examples, one or more markers may be used to examine and/or evaluate genetic characteristics of a cotton variety. Particular markers used for these purposes are not limited to any particular set of markers and diagnostic platforms, but are envisioned to include any type of markers and diagnostic platforms that can provide means for distinguishing varieties. One method of genetic characterization may to use only homozygous loci for cotton variety GW-13-1409.

Primers and PCR protocols for assaying these and other markers are disclosed in, for example, CottonGen located on the World Wide Web at cottongen.org. In addition to being used for identification of cotton variety GW-13-1409, as well as plant parts and plant cells of cotton variety GW-13-1409, a genetic profile may be used to identify a cotton plant produced through the use of cotton variety GW-13-1409 or to verify a pedigree for progeny plants produced through the use of cotton variety GW-13-1409. A genetic marker profile may also be useful in breeding and developing backcross conversions.

In an embodiment, a cotton plant is provided for that is characterized by molecular and physiological data obtained from a representative sample of said variety deposited with a depository. Thus, plants, seeds, or parts thereof, having all or essentially all of the morphological and physiological characteristics of cotton variety GW-13-1409 are provided. Further provided is a cotton plant formed by the combination of the disclosed cotton plant or plant cell with another cotton plant or cell and comprising the homozygous alleles of the variety.

In some examples, a plant, a plant part, or a seed of cotton variety GW-13-1409 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

One means of performing genetic marker profiling is using SSR polymorphisms that are well known in the art. A marker system based on SSRs can be highly informative in linkage analysis relative to other marker systems, in that multiple alleles for a given locus may be present. Another advantage of this type of marker is that through use of flanking primers, collecting more informative SSR data can be relatively easily achieved, for example, by using the polymerase chain reaction (PCR), thereby eliminating the need for labor-intensive Southern hybridization. PCR detection may be performed using two oligonucleotide primers flanking the polymorphic segment of repetitive DNA to amplify the SSR region.

Following amplification, genotype of test material revealed by each marker can be scored by electrophoresis of the amplification products. Scoring of marker genotype is based on the size of the amplified fragment, which correlates to the number of base pairs of the fragment. While variation in the primer used or in the laboratory procedures can affect the reported fragment size, relative values should remain constant regardless of specific primer or laboratory used. When comparing varieties, it may be beneficial to have all profiles performed in the same lab. Primers that can be used are publicly available and may be found in, for example, CottonGen (Yu et al., CottonGen: a genomics, genetics and breeding database for cotton research," Nucleic Acids Research 42 (D1):D1229-D1236, 2013).

A genotypic profile of cotton variety GW-13-1409 can be used to identify a plant comprising variety GW-13-1409 as a parent, since such plants will comprise the same homozygous alleles as variety GW-13-1409. Because the cotton variety at inbred stage is essentially homozygous at all relevant loci, most loci should have only one type of allele present. In contrast, a genetic marker profile of an $F_1$ progeny should be the sum of those parents, e.g., if one parent was homozygous for allele X at a particular locus, and the other parent homozygous for allele Y at that locus, then the $F_1$ progeny will be XY (heterozygous) at that locus. Subsequent generations of progeny produced by selection and breeding are expected to be of genotype XX (homozygous), YY (homozygous), or XY (heterozygous) for that locus position. When the $F_1$ plant is selfed or sibbed for successive filial generations, the locus should be either X or Y for that position.

In addition, plants and plant parts substantially benefiting from the use of variety GW-13-1409 in their development, such as variety GW-13-1409 comprising a backcross conversion, transgene, or genetic sterility factor, may be identified by having a molecular marker profile with a high percent identity to cotton variety GW-13-1409. Such a percent identity might be 90%, 91%, 92%, 93%, 94%, 95%, 96%, 97%, 98%, 99%, 99.5% or 99.9% identical to cotton variety GW-13-1409.

A genotypic profile of variety GW-13-1409 also can be used to identify essentially derived varieties and other progeny varieties developed from the use of variety GW-13-1409, as well as cells and other plant parts thereof. Plants of the embodiments include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of variety GW-13-1409 when grown under the same conditions. Such plants may be developed using markers well known in the art. Progeny plants and plant parts produced using variety GW-13-1409 may be identified, for example, by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from cotton variety GW-13-1409, as measured by either percent identity or percent similarity. Such progeny may be further characterized as being within a pedigree distance of variety GW-13-1409, such as within 1, 2, 3, 4, or 5 or less cross pollinations to a cotton plant other than variety GW-13-1409, or a plant that has variety GW-13-1409 as a progenitor. Unique molecular profiles may be identified with other molecular tools, such as SNPs and RFLPs.

Mutation Breeding

Mutation breeding is another method of introducing new traits into GW-13-1409. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanies by the isolation of chromosomal DNA from every mutated plant line or seed and screening of the population of the seed or plants is performed at the DNA level using advanced molecular techniques; zinc finger nucleases. Once a desired trait is observed through mutagenesis the trait may then be incorporated into existing germplasm by traditional breeding techniques. Example details of mutation breeding can be found in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" *International Journal of Plant Genomics.* 2011 (2011); 13 pages; Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015). In addition, mutations created in other cotton plants may be used to produce a backcross conversion of cotton plants that comprises such mutation. Another embodiment includes spontaneously or naturally induced or artificially induced mutations to the cotton plant of GW-13-1409. Further embodiments include mutations consisting of temperature, long-term seed storage, tissue culture conditions, ionizing radiation, chemical mutagens, or targeting induced local lesions in genomes, and wherein the resulting plant comprises at least one genome mutation of the cotton plant of GW-13-1409.

Double Haploid/Haploid Breeding

Double haploid methods can also be used to obtain a cotton plant that is homozygous at essentially every locus, wherein the cotton plant received all of its alleles from the progeny cotton plant having cotton variety GW-13-1409 as a parent. In other embodiments, a progeny plant having cotton variety GW-13-1409 as a parent is crossed with a different cotton plant that may include any cotton plant that is not cotton variety GW-13-1409, any cotton plant that does not have cotton variety GW-13-1409 2 as a parent, another germplasm source, a haploid or mutation inducing stock, or a trait donor plant, thereby providing a set of distinct, pure-breeding inbred lines. The resulting inbred lines could then be crossed with other inbred or non-inbred lines and the resulting inbred progeny analyzed for beneficial characteristics. In this way, novel inbred lines conferring desirable characteristics could be identified.

Gene Editing Using CRISPR

Targeted gene editing can be done using CRISPR/Cas9 technology (Saunders & Joung, *Nature Biotechnology,* 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system. See for example, U.S. Application Publication No. WO2014068346 (Gyorgy et al., Identification of a *Xanthomonas euvesicatoria* resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science* Vol. 7 Nov. 2016; and "Exploiting the CRISPR/Cas9 System for Targeted Genome Mutagenesis in *Petunia*" *Science Reports* Volume 6: February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on cotton GW-13-1409 to modify traits and resistances or tolerances to pests, herbicides, diseases, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on cotton variety GW-13-1409 to modify traits and resistances or tolerances to pests, herbicides, and viruses.

Transformation

Many useful traits are those which are introduced by genetic transformation techniques. Methods for the genetic transformation of cotton are known to those of skill in the art, (see, e. g. Firoozabady et al., Plant Mol. Biol., 10:105-116, 1987). For example, broadly applicable plant transformation methods which have been described include *Agrobacterium*-mediated transformation, microprojectile bombardment, electroporation, and direct DNA uptake by protoplasts.

*Agrobacterium*-mediated transfer is a widely applicable system for introducing gene loci into plant cells, including cotton. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Bio. Tech., 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., Bio. Tech., 3(7):629-635, 1985; U.S. Pat. No. 5,563,055). One efficient means for transformation of cotton in particular is transformation and regeneration of cotton hypocotyl explants following inoculation with *Agrobacterium tumefaciens* from primary callus development, embryogenesis, embryogenic callus identification, transgenic cotton shoot production and the development of transgenic plants, as is known in the art.

To effect transformation by electroporation, for example, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. Protoplasts may also be employed for electroporation transformation of plants (Bates, Mol. Biotechnol., 2(2):135-145, 1994; Lazzeri, Methods Mol. Biol., 49:95-106, 1995). For example, the generation of transgenic cotyledon-derived protoplasts was described by Dhir and Widholm in Intl. Patent Appl. Publ. No. WO 92/17598, the disclosure of which is specifically incorporated herein by reference. When protoplasts are used, transformation can also be achieved using methods based on calcium phosphate precipitation, polyethylene glycol treatment, and combinations of these treatments (see, e.g., Potrykus et al., Mol. Gen. Genet., 199(2):169-177, 1985; Omirulleh et al., Plant Mol. Biol., 21(3):415-428, 1993; Fromm et al., Nature, 319(6056):791-793, 1986; Uchimiya et al., Mol. Gen. Genet., 204(2):204-207, 1986; Marcotte and Bayley, Nature, 335(6189):454-457, 1988).

Microprojectile bombardment is another efficient method for delivering transforming DNA segments to plant cells. In this method, particles are coated with nucleic acids and delivered into cells by a propelling force. Exemplary particles include those comprised of tungsten, platinum, and often, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

Microprojectile bombardment techniques are widely applicable, and may be used to transform virtually any plant species. The application of microprojectile bombardment for the transformation of cotton is described, for example, in Rajasekaran et al., Mol. Breed., 2:307-319, 1996. An illustrative embodiment of a method for microprojectile bombardment is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Included among various plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Expression Vectors for Cotton Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol.* Rep., 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for Cotton Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J Cell. Biol.*, 108:1657 (1989); Creissen, et al., *Plant* 1, 2:129 (1991); Kalderon, et al., *Cell*, 39:499-509 (1984); Steifel, et al., *Plant Cell*, 2:785-793 (1990).

Gene Silencing

Many techniques for gene silencing are well-known to one of skill in the art, including, but not limited to, knockouts (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

Additional Transformation Embodiments

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

It is understood to those of skill in the art that a locus of transgenic origin need not be directly transformed into a plant, as techniques for the production of stably transformed cotton plants that pass single loci to progeny by Mendelian inheritance is well known in the art. Such single loci may therefore be passed from parent plant to progeny plants by standard plant breeding techniques that are well known in the art. Non-limiting examples of traits that may be introduced directly or by backcrossing are presented below.

Male Sterility

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile F$_1$ hybrid progeny. If no restorer gene is present in the male parent, male-sterile hybrids are obtained. Examples of male-sterility genes and corresponding restorers which could be employed with the plants of the embodiments are well known to those of skill in the art of plant breeding. Examples of such genes include CMS-D2-2, CMS-hir, CMS-D8, CMS-D4, and CMS-C1. Fertility can be restored to CMS-D2-2 by the D2 restorer in which the restorer factor(s) was introduced from the genome of *G. harknessii* Brandegee (D2-2). Microsporogenesis in both CMS systems aborts during the premeiotic stage. One dominant restorer gene from the D8 restorer was identified to restore fertility of CMS-D8. The D2 restorer for CMS-D2-2 also restores the fertility of CMS-D8, CMS-hir, and CMS-C1.

Herbicide Tolerance

Numerous herbicide tolerance genes are known and may be employed with embodiments of the invention. A non-limiting example is a gene conferring resistance to an herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., EMBO J., 7:1241, 1988; Gleen et al., Plant Molec. Biology, 18:1185-1187, 1992; and Miki et al., Theor. Appl. Genet., 80:449, 1990. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. No. 4,940,835 to Shah et al., which discloses the nucleotide sequence of a form of EPSPS that can confer glyphosate resistance. Non-limiting examples of EPSPS transformation events conferring glyphosate resistance are provided by U.S. Pat. Nos. 6,040,497 and 7,632,985. The MON89788 event disclosed in U.S. Pat. No. 7,632,985 in particular is beneficial in conferring glyphosate tolerance in combination with an increase in average yield relative to prior events A DNA molecule encoding a mutant aroA gene can be obtained under ATCC Accession No. 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al., Plant Cell Reports, 14:482-487, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246 to Leemans et al. DeGreef et al. (Biotechnology, 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes described by Marshall et al., (Theon. Appl. Genet., 83:435-442, 1992). As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil. Przibila et al. (Plant Cell, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (Biochem. J., 285(1):173-180, 1992). 4-hydroxyphenylpyruvate dioxygenase (HPPD) is a target of the HPPD-inhibiting herbicides, which deplete plant plastoquinone and vitamin E pools. Rippert et al. (Plant Physiol., 134:92-100, 2004) describes an HPPD-inhibitor resistant tobacco plant that was transformed with a yeast-derived prephenate dehydrogenase (PDI-1) gene.

Protoporphyrinogen oxidase (PPO) is the target of the PPO-inhibitor class of herbicides; a PPO-inhibitor resistant PPO gene was recently identified in *Amaranthus tuberculatus* (Patzoldt et al., PNAS, 103(33):12329-12334, 2006).

The herbicide methyl viologen inhibits $CO_2$ assimilation. Foyer et al. (Plant Physiol., 109:1047-1057, 1995) describe a plant overexpressing glutathione reductase (GR) that is resistant to methyl viologen treatment.

Siminszky (Phytochemistry Reviews, 5:445-458, 2006) describes plant cytochrome P450-mediated detoxification of multiple, chemically unrelated classes of herbicides. Modified bacterial genes have been successfully demonstrated to confer resistance to atrazine, an herbicide that binds to the plastoquinone-binding membrane protein $Q_B$ in photosystem II to inhibit electron transport. See, for example, studies by Cheung et al. (PNAS, 85(2):391-395, 1988), describing tobacco plants expressing the chloroplast psbA gene from an atrazine-resistant biotype of *Amaranthus hybridus* fused to the regulatory sequences of a nuclear gene, and Wang et al. (Plant Biotech. J., 3:475-486, 2005), describing transgenic alfalfa, *Arabidopsis*, and tobacco plants expressing the atzA gene from *Pseudomonas* sp. that were able to detoxify atrazine.

Bayley et al. (Theor. Appl. Genet., 83:645-649, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Pseudomonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448, 476; 6,248,876; 6,225,114; 6,107,549; 5,866,775; 5,804, 425; 5,633,435; 5,463,175.

Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science, 266:789, 1994 (cloning of the tomato Cf-9 gene for resistance to *Cladosporium flavum*); Martin et al., Science, 262:1432, 1993 (tomato Pto gene for resistance to *Pseudomonas syringae* pv.); Mindrinos et al., Cell, 78:1089, 1994 (*Arabidopsis* RPS2 gene for resistance to *Pseudomonas syringae*). Logemann et al., (Bio/technology, 10:305, 1992), for example, disclose transgenic plants expressing a barley ribosome-inactivating gene have an increased resistance to fungal disease.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol., 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody may also be used. See, for example, Tavladoraki et al., (Nature, 366:469, 1993), who show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or increasing salicylic acid production (Ryals et al., Plant Cell, 8:1809-1819, 1996).

Plant defensins may be used to provide resistance to fungal pathogens (Thomma et al., Planta, 216:193-202, 2002).

Nematode resistance has been described, for example, in U.S. Pat. No. 6,228,992 and bacterial disease resistance in U.S. Pat. No. 5,516,671.

Insect Resistance

One example of an insect resistance gene includes a *Bacillus thuringiensis* protein, a derivative thereof, or a synthetic polypeptide modeled thereon. See, for example, Geiser et al., (Gene, 48:109, 1986), who disclose the cloning and nucleotide sequence of a Bt Δ-endotoxin gene. Moreover, DNA molecules encoding Δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (Plant Molec. Biol., 24:25, 1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., J. Biol. Chem., 262:16793, 1987 (nucleotide sequence of rice cysteine proteinase inhibitor), Huub et al., Plant Molec. Biol., 21:985, 1993 (nucleotide sequence of cDNA encoding tobacco proteinase inhibitor I), and Sumitani et al., Biosci. Biotech. Biochem., 57:1243, 1993 (nucleotide sequence of *Streptomyces nitrosporeus* alpha-amylase inhibitor).

An insect-specific hormone or pheromone may also be used. See, for example, Hammock et al., (Nature, 344:458, 1990) disclosing baculovirus expression of cloned juvenile hormone esterase, an inactivator of juvenile hormone, Gade and Goldsworthy (Eds. Physiological System in Insects, Elsevier Academic Press, Burlington, Mass., 2007), describing allostatins and their potential use in pest control; and Palli et al. (Vitam. Horm., 73:59-100, 2005), disclosing use of ecdysteroid and ecdysteroid receptor in agriculture. The diuretic hormone receptor (DHR) was identified in Price et al. (Insect Mol. Biol., 13:469-480, 2004) as a candidate target of insecticides.

Still other examples include an insect-specific antibody or an immunotoxin derived therefrom and a developmental-arrestive protein. See Taylor et al., (Seventh Int'l Symposium on Molecular Plant-Microbe Interactions (Edinburgh, Scotland) Abstract #497, 1994), who described enzymatic inactivation in transgenic tobacco via production of single-chain antibody fragments.

Resistance to Abiotic Stresses

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobacter globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levansucrase (SacB) from yeast and *Bacillus subtilis*, respectively, can provide protection against drought (summarized from Annex II Genetic Engineering for Abiotic Stress Tolerance in Plants, Consultative Group on International Agricultural Research Technical Advisory Committee). Overexpression of superoxide dismutase can be used to protect against superoxides, as described in U.S. Pat. No. 5,538,878 to Thomas et al.

Modified Fatty Acid, Phytate, and Carbohydrate Metabolism

Genes may be used conferring modified fatty acid metabolism. For example, stearyl-ACP desaturase genes may be used. See Knutzon et al., Proc. Natl. Acad. Sci. USA, 89:2624, 1992. Various fatty acid desaturases have also been described, such as a *Saccharomyces cerevisiae* OLE1 gene encoding delta-9 fatty acid desaturase, an enzyme which forms the monounsaturated palmitoleic (16:1) and oleic (18:1) fatty acids from palmitoyl (16:0) or stearoyl (18:0) CoA (McDonough et al., J. Biol. Chem., 267(9):5931-5936, 1992); a gene encoding a stearoyl-acyl carrier protein .DELTA.9 desaturase from castor (Fox et al. Proc. Natl. Acad. Sci. USA, 90(6):2486-2490, 1993); .DELTA.6 and .DELTA.12 desaturases from the cyanobacteria *Synechocystis* responsible for the conversion of linoleic acid (18:2) to gamma-linolenic acid (18:3 gamma) (Reddy et al. Plant Mol. Biol., 22(2):293-300, 1993); a gene from *Arabidopsis thaliana* that encodes an omega-3 desaturase (Arondel et al. Science, 258(5086):1353-1355, 1992); plant A9 desaturases (PCT Application Publ. No. WO 91/13972) and soybean and *Brassica* A15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (Gene, 127:87, 1993), for a disclosure of the nucleotide sequence of an *Aspergillus niger* phytase gene. This, for example, could be accomplished by cloning and then reintroducing DNA associated with the single allele which is responsible for mutants characterized by low levels of phytic acid. See Raboy et al., (Maydica, 35:383, 1990).

A number of genes are known that may be used to alter carbohydrate metabolism. For example, plants may be transformed with a gene coding for an enzyme that alters the branching pattern of starch. See Shiroza et al., J. Bacteol., 170:810, 1988 (nucleotide sequence of *Streptococcus mutans* fructosyltransferase gene), Steinmetz et al., Mol. Gen. Genet., 20:220, 1985 (nucleotide sequence of *Bacillus subtilis* levansucrase gene), Pen et al., BioTechnology, 10:292, 1992 (production of transgenic plants that express *Bacillus licheniformis* alpha-amylase), Elliot et al., Plant Molec. Biol., 21:515, 1993 (nucleotide sequences of tomato invertase genes), Sergaard et al., J. Biol. Chem., 268:22480, 1993 (site-directed mutagenesis of barley alpha-amylase gene), and Fisher et al., Plant Physiol., 102:1045, 1993 (maize endosperm starch branching enzyme II). The Z10 gene encoding a 10 kD zein storage protein from maize may also be used to alter the quantities of 10 kD zein in the cells relative to other components (Kirihara et al., Mol. Gen. Genet., 211:477-484, 1988).

Improved Cotton Fiber Characteristics

Fiber characteristics such as fiber quality of quantity represent another example of a trait that may be modified in cotton varieties. For example, U.S. Pat. No. 6,472,588 describes transgenic cotton plants transformed with a sucrose phosphate synthase nucleic acid to alter fiber characteristics such as strength, length, fiber fineness, fiber maturity ratio, immature fiber content, fiber uniformity, and micronaire. Cotton plants comprising one or more genes coding for an enzyme selected from the group consisting of endoxyloglucan transferase, catalase and peroxidase for the improvement of cotton fiber characteristics are also described in U.S. Pat. No. 6,563,022. Cotton modification using ovary-tissue transcriptional factors preferentially directing gene expression in ovary tissue, particularly in very early fruit development, utilized to express genes encoding isopentenyl transferase in cotton ovule tissue and modify the characteristics of boll set in cotton plants and alter fiber quality characteristics including fiber dimension and strength is discussed in U.S. Pat. No. 6,329,570. A gene controlling the fiber formation mechanism in cotton plants is described in U.S. Pat. No. 6,169,174.

Genes involved in lignin biosynthesis are described by Dwivedi et al., Mol. Biol., 26:61-71, 1994; Tsai et al., Physiol., 107:1459, 1995; U.S. Pat. No. 5,451,514 (claiming the use of cinnamyl alcohol dehydrogenase gene in an antisense orientation such that the endogenous plant cinnamyl alcohol dehydrogenase gene is inhibited).

Additional Traits

Additional traits can be introduced into the cotton variety of one or more embodiments. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the cotton variety GW-13-1409 is a sequence which allows for site-specific recombination. Examples of such sequences include the FRT sequence, used with the FLP recombinase (Zhu and Sadowski, J. Biol. Chem., 270:23044-23054, 1995); and the LOX sequence, used with CRE recombinase (Sauer, Mol. Cell. Biol., 7:2087-2096, 1987). The recombinase genes can be encoded at any location within the genome of the cotton plant, and are active in the hemizygous state.

It may also be desirable to make cotton plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, Microbiology & Mol. Biol. Reviews, 67:16-37, 2003).

Tissue Cultures and In Vitro Regeneration of Cotton Plants

A further aspect relates to tissue cultures of the cotton variety designated GW-13-1409. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, ovules, pollen, seeds, petiole, shoot, stem, cotyledons, hypocotyl, protoplasts, meristematic cells, callus, flowers, leaves, roots, root tips, anthers, and the like. In one embodiment, the tissue culture comprises embryos, protoplasts, meristematic cells, pollen, leaves or anthers. Means for preparing and maintaining plant tissue culture are well-known in the art.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Plants typically are regenerated via two distinct processes; shoot morphogenesis and somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an induction step may not give rise to rapidly-growing proliferative cultures. Therefore, it may be desired to optimize tissue culture conditions for each cotton line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, pollen, leaves, ovules, anthers, cotyledons, hypocotyl, pistils, roots, root tips, flowers, seeds, petiole, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

A deposit of the Golden West Research Ltd. proprietary cotton variety GW-13-1409 disclosed above and recited in the appended claims has been made with the National Collections of Industrial, Food and Marine Bacteria (NCIMB), Ferguson Building, Craibstone Estate, Bucksburn, Aberdeen, AB21 9YA, Scotland, United Kingdom. The date of deposit was Jun. 14, 2021. The NCIMB No. is 43793. The deposit of at least 625 seeds was taken from the same deposit maintained by Golden West Research Ltd. since prior to the filing date of this application. The deposit will be maintained in the NCIMB depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A seed of cotton variety designated GW-13-1409, wherein a representative sample seed of the variety was deposited under NCIMB No. 43793.

2. A method for producing cotton seed, comprising:
planting the seed of claim 1;
growing a plant from the seed under pollinating conditions; and
harvesting the resultant seed.

3. Cotton seed produced by the method of claim 2.

4. A cotton plant, or a regenerable part thereof, produced by growing the seed of claim 1.

5. A tissue or cell culture of regenerable cells produced from the plant of claim 4.

6. The plant part of claim 4, wherein said plant part is selected from the group consisting of a cell, meristematic cell, a protoplast, pods, callus, an embryo, pollen, an ovule, pistils, stems, flower, seed, leaf, root, root tip, and anther.

7. A method for producing a cotton plant, comprising crossing cotton variety GW-13-1409, wherein a representative sample of seed of the variety was deposited under NCIMB No. 43793, with another different cotton plant to yield progeny cotton seed.

8. A cotton plant produced by the method of claim 7.

9. A method of introducing a desired trait into cotton variety GW-13-1409, wherein a representative sample of seed of the variety was deposited under NCIMB No. 43793, comprising:
(a) crossing GW-13-1409 plants with plants of another cotton variety that comprise a desired trait to produce progeny plants;
(b) selecting progeny plants that have the desired trait;
(c) crossing selected progeny plants with GW-13-1409 plants to produce backcross progeny plants;
(d) selecting for backcross progeny plants that comprise the desired trait; and
(e) repeating steps (c) and (d) at least three or more times in succession to produce the selected fourth and higher backcross progeny plants that comprise the desired trait and essentially all of the physiological and morphological characteristics of cotton variety GW-13-14092 listed in Table 1.

10. A cotton seed produced by the method of claim 9.

11. A cotton plant produced by growing the cotton seed of claim 10.

12. The seed of claim 1, further comprising a coating.

13. A method of producing a cotton plant resistant to the group consisting of herbicides, insecticides, and disease, wherein the method comprises transforming the plant of claim 4 with a transgene, and wherein said transgene confers resistance to an herbicide, insecticide, or disease.

14. An herbicide, insecticide, or disease resistant plant produced by the method of claim 13.

15. A method for developing a cotton plant in a plant breeding program, comprising applying plant breeding techniques comprising crossing, outcrossing, recurrent selection, mutation breeding, wherein said mutation breeding selects for a mutation that is spontaneously or naturally induced or artificially induced, backcrossing, pedigree breeding, marker enhanced selection, haploid/double haploid production, or transformation to the cotton plant of claim 4, or its parts, wherein application of said techniques results in development of a cotton plant.

16. A method of introducing a mutation into the genome of a cotton plant GW-13-1409, said method comprising mutagenesis of the plant, or plant part thereof, of claim 4, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

17. A method of editing the genome of cotton variety plant GW-13-1409 of claim 4, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

18. A cotton plant produced by the method of claim 17.

19. A method of producing a commodity plant product, said method comprising using the plant of claim 4 to produce a commodity plant product.

20. The method of claim 19, wherein said commodity plant product is lint, seed oil, or seed.

* * * * *